United States Patent
Craig et al.

(10) Patent No.: US 8,796,269 B2
(45) Date of Patent: Aug. 5, 2014

(54) **CRYSTALLINE 2-(3,5-BIS(TRIFLUORO-METHYL)PHENYL)-*N*-(4-(4-FLUORO-2-METHYLPHENYL)-6-((7*S*,9A*S*)-7-(HYDROXYMETHYL)HEXAHYDRO-PYRAZINO[2,1-*C*][1,4]OXAZIN-8(1*H*)-YL)PYRIDIN-3-YL)-*N*,2-DIMETHYL-PROPANAMIDE OF THE FORMULA (I), THEIR USE IN THERAPY, AND PROCESS FOR THE PREPARATION OF THE SAME**

(75) Inventors: Andrew Simon Craig, Stevenage (GB); Salima Zarah Ismail, Stevenage (GB); Ronnie Maxwell Lawrence, Stevenage (GB)

(73) Assignee: Nerre Therapeutics Limited, London (GB)

( * ) Notice: Subject to any disclaimer, the term of this patent is extended or adjusted under 35 U.S.C. 154(b) by 39 days.

(21) Appl. No.: 13/389,525

(22) PCT Filed: Aug. 25, 2010

(86) PCT No.: PCT/EP2010/062420
§ 371 (c)(1),
(2), (4) Date: Mar. 5, 2012

(87) PCT Pub. No.: WO2011/023733
PCT Pub. Date: Mar. 3, 2011

(65) Prior Publication Data
US 2012/0157450 A1    Jun. 21, 2012

Related U.S. Application Data

(60) Provisional application No. 61/237,435, filed on Aug. 27, 2009.

(51) Int. Cl.
*A61K 31/444*    (2006.01)
*A61K 31/4985*   (2006.01)
*C07D 213/72*    (2006.01)
*C07D 498/04*    (2006.01)

(52) U.S. Cl.
CPC .................................. *C07D 498/04* (2013.01)
USPC ............ 514/249; 514/352; 544/350; 546/309

(58) Field of Classification Search
CPC ............ A61K 31/444; A61K 31/4985; C07D 213/72; C07D 498/04
USPC .................... 514/249, 352; 544/350; 546/309
See application file for complete search history.

(56) References Cited

FOREIGN PATENT DOCUMENTS

| WO | 2007028654 A1 | 3/2007 |
|----|---------------|--------|
| WO | 2010015626 A1 | 2/2010 |

OTHER PUBLICATIONS

Stahly, G.P., "Diversity in Single- and Multiple-Component Crystals. The Search for and Prevalence of Polymorphs and Cocrystals", Crystal Growth and Design, 2007, vol. 7, No. 6, pp. 1007-1026.

*Primary Examiner* — Douglas M Willis
(74) *Attorney, Agent, or Firm* — Steinfl & Bruno, LLP

(57) ABSTRACT

The invention relates to the compound of formula (I) in a crystalline anhydrate form,

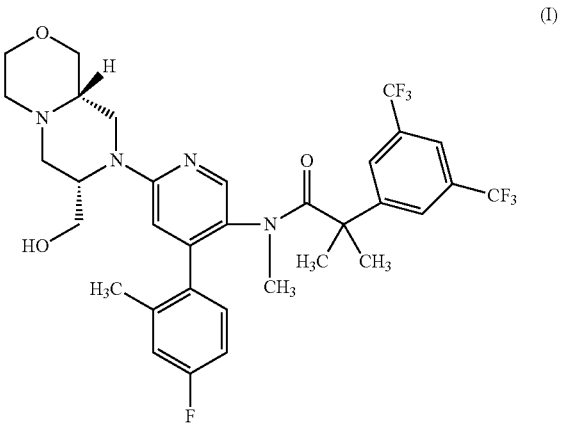

pharmaceutical formulations containing them, their use in therapy and processes for preparing the same.

9 Claims, 3 Drawing Sheets

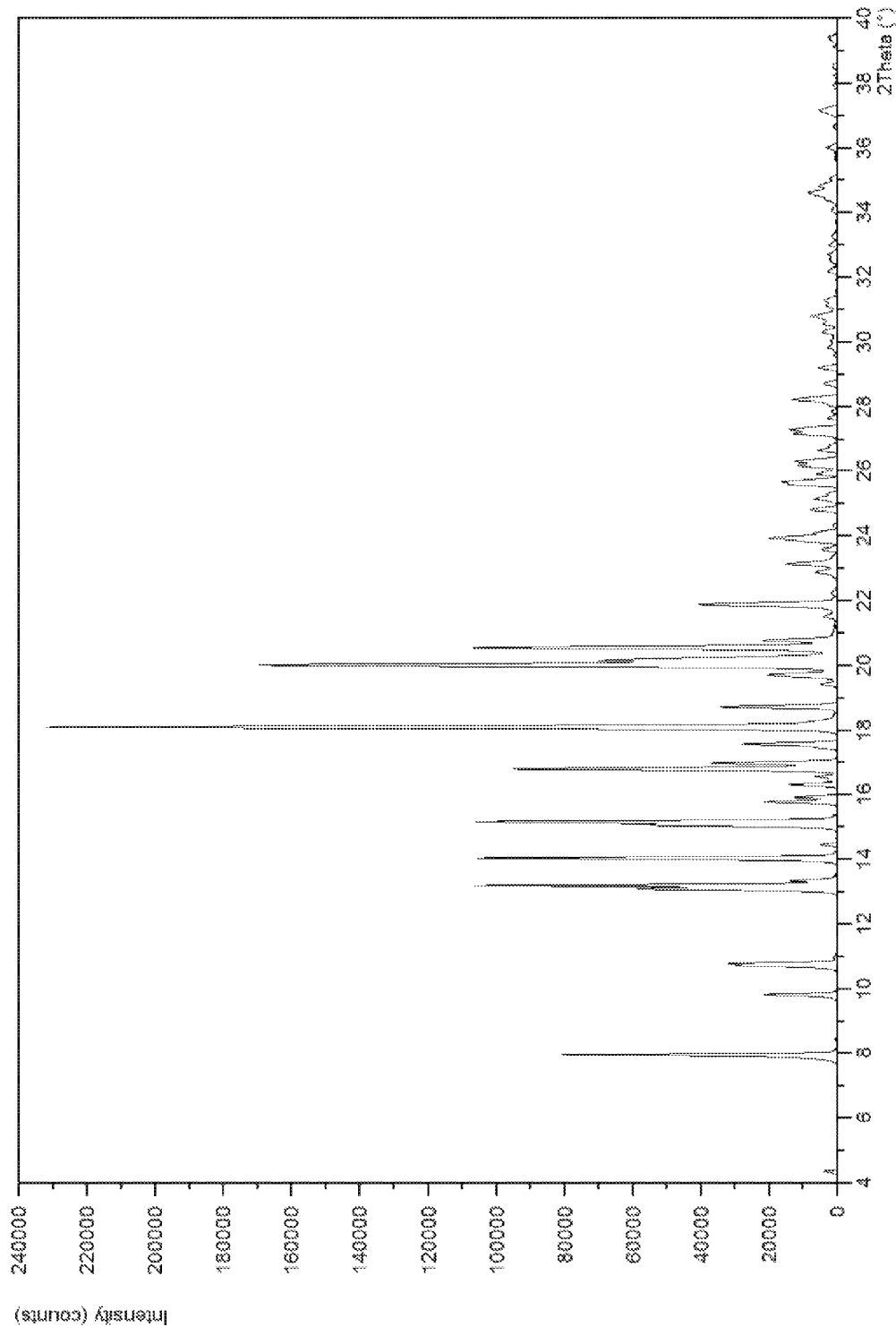
Figure 1 – XPRD pattern of the compound of formula (I) in crystalline anhydrate form 1

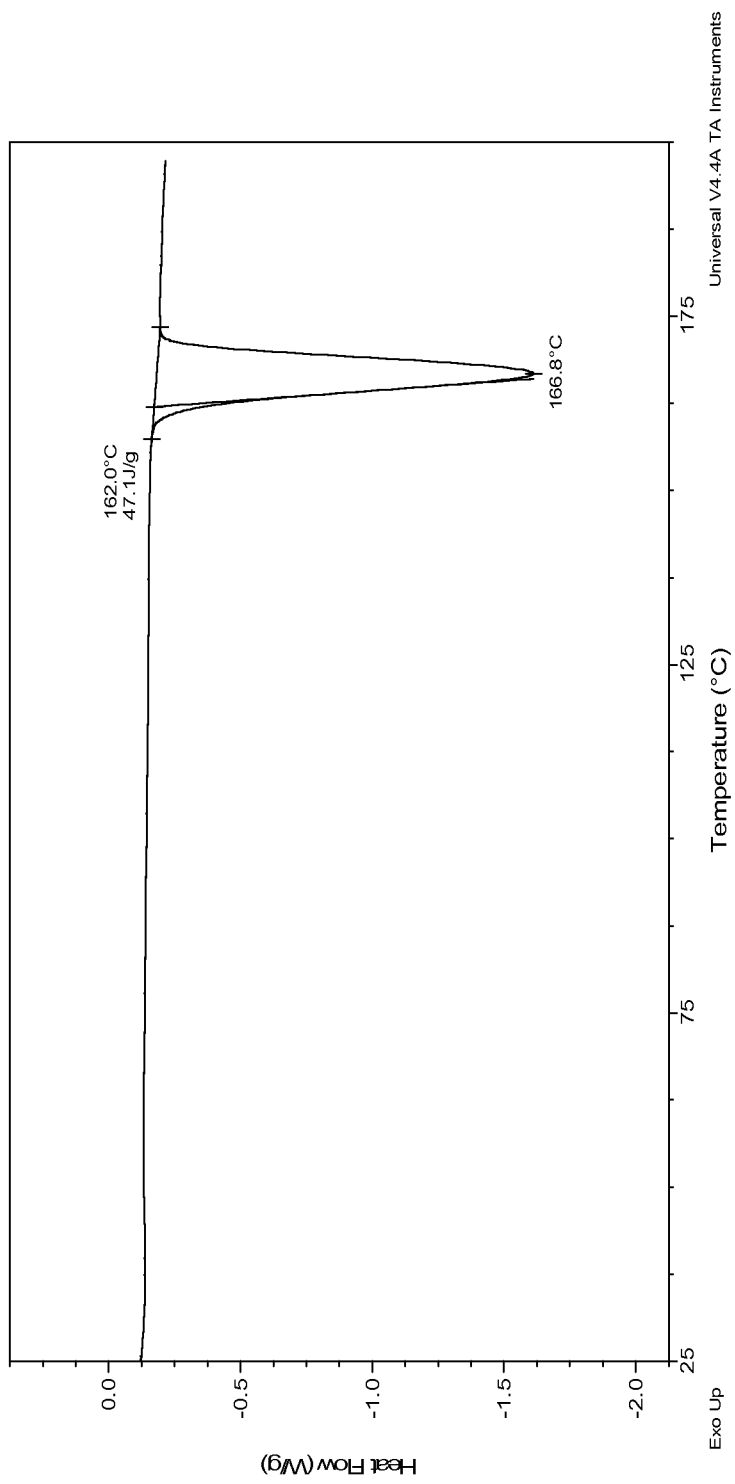
Figure 2. DSC thermogram of the compound of formula(I) in crystalline anhydrate Form 1

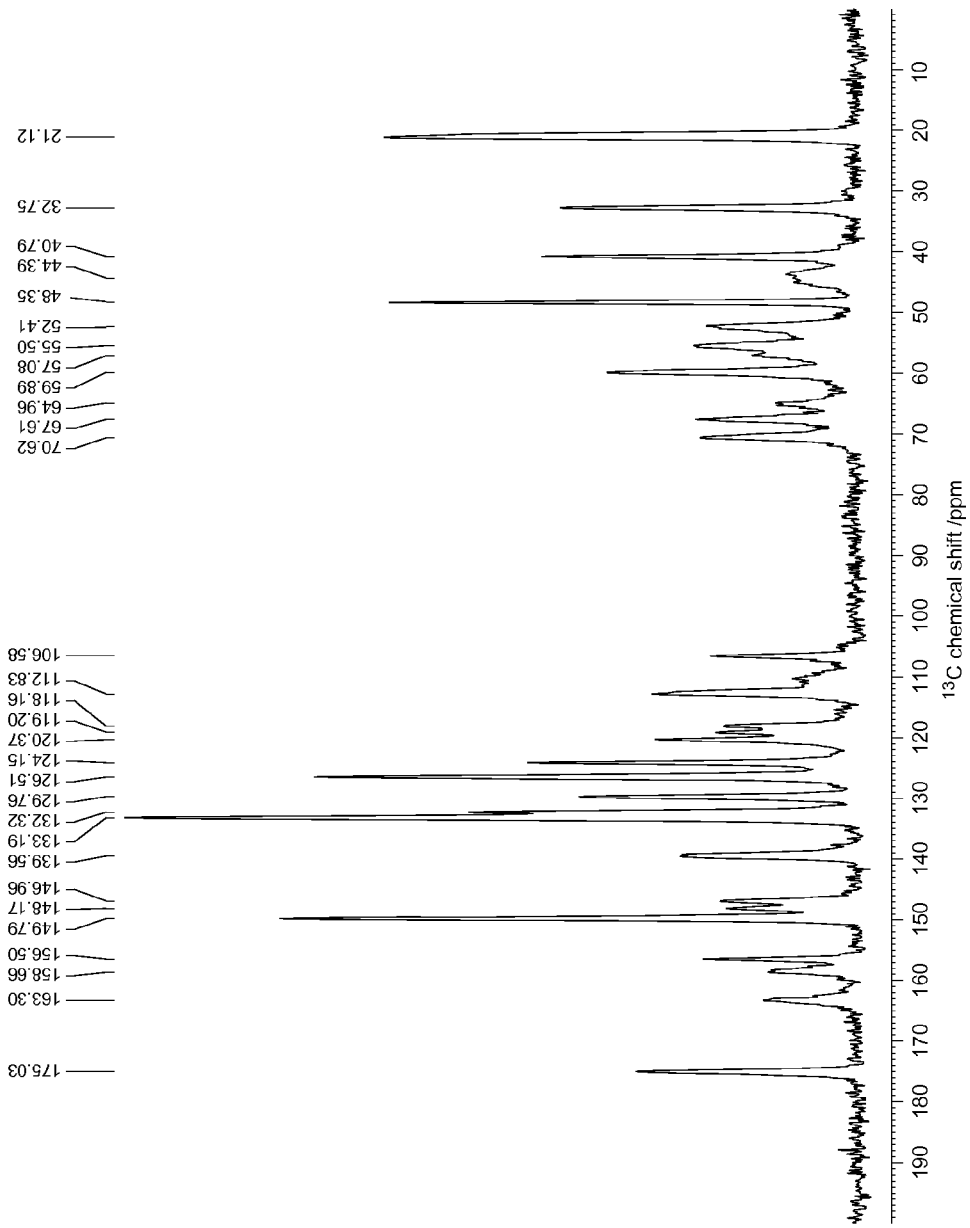
Figure 3: SSNMR spectrum of the compound of formula(I) in crystalline anhydrate Form 1

CRYSTALLINE 2-(3,5-BIS(TRIFLUORO-METHYL)PHENYL)-N-(4-(4-FLUORO-2-METHYLPHENYL)-6-((7S,9AS)-7-(HYDROXYMETHYL)HEXAHYDRO-PYRAZINO[2,1-C][1,4]OXAZIN-8(1H)-YL)PYRIDIN-3-YL)-N,2-DIMETHYL-PROPANAMIDE OF THE FORMULA (I), THEIR USE IN THERAPY, AND PROCESS FOR THE PREPARATION OF THE SAME

CROSS-REFERENCE TO RELATED APPLICATIONS

This application is filed pursuant to 35 USC 371 as a United States National Phase Application of International Patent Application Serial No. PCT/EP2010/062420 filed on Aug. 25, 2010, which claims priority from 61/237,435 filed on Aug. 27, 2009 in the United States.

FIELD OF THE INVENTION

The present invention relates to crystalline anhydrate forms of 2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide, pharmaceutical formulations containing them, their use in therapy and processes for preparing the same. This compound is an antagonist of the NK1 and NK3 receptors and thus may be of use in the treatment of psychotic disorders, depression, mood disorders, anxiety, sleep disorders and substance-related disorders.

BACKGROUND OF THE INVENTION

WO07/028654 describes a number of pyridine derivatives or pharmaceutical acceptable salts thereof as antagonists of the NK1 and NK3 receptors and thus may be of use in the treatment of psychotic disorders. In particular, the compound 2-[3,5-Bis(trifluoromethyl)phenyl]-N-{4-(4-fluoro-2-methyl phenyl)-6-[(7S,9aS)-7-(hydroxymethyl)hexahydropyrazino[2,1-c][1,4]oxazin-8(1H)-yl]-3-pyridinyl}-N,2-dimethylpropanamide or pharmaceutical acceptable salts thereof are described in WO07/028654.

Hydrochloride salt of 2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide is also described in WO07/028654.

The structure of 2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide is shown in formula (I) below.

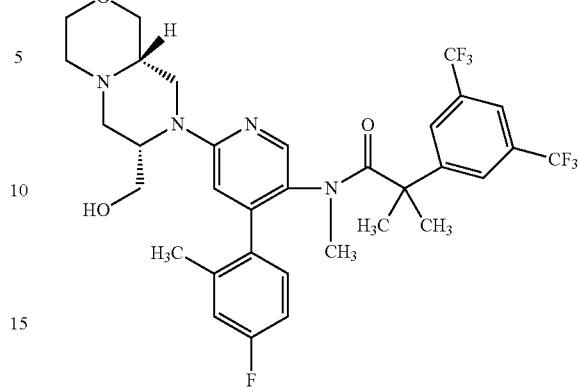

(I)

Pharmaceutical acceptable salts of the compound of formula (I) include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and 4-methyl benzenesulfonic acids.

The compound of formula (I) or its hydrochloride are obtained, according to the procedure described in WO07/028654, as partially amorphous or wholly amorphous solids and it is hygroscopic. Amorphous solids and particularly hygroscopic solids are difficult to handle under pharmaceutical processing conditions typically because of low bulky densities and unsatisfactory flow properties.

Accordingly, a need exists for crystalline forms of the compound of formula (I) with superior physiochemical properties that may be used advantageously in pharmaceutical processing and pharmaceutical compositions.

SUMMARY OF THE INVENTION

We have now found a crystalline anhydrate form of 2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide having (Formula (I)

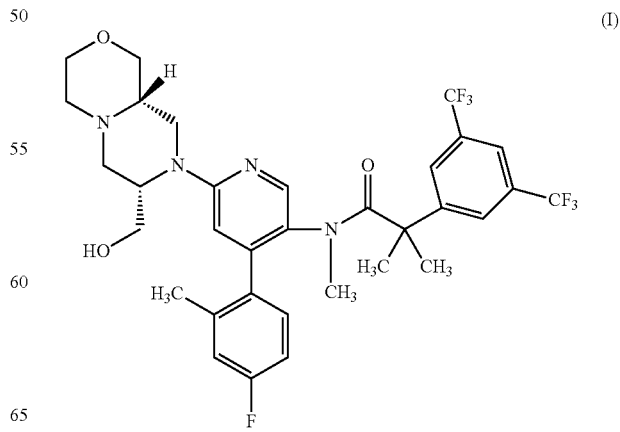

(I)

In a first aspect of the invention, there is provided the compound of formula (I) in a crystalline anhydrate form.

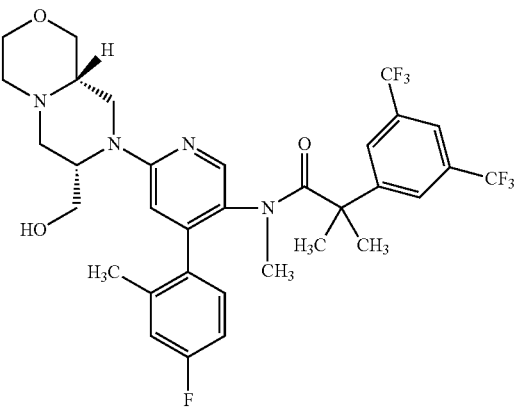

(I)

In a second aspect of the invention, there is provided the compound of formula (I) in crystalline anhydrate Form 1.

In a third aspect of the present invention, there is provided the compound of formula (I) in crystalline anhydrate Form 1, wherein the XRPD pattern is expressed in terms of 2 theta angles and obtained with a diffractometer using copper Kα X-radiation.

In a fourth aspect of the present invention, there is provided the compound of formula (I) in crystalline anhydrate Form 1, characterized by substantially the same X-ray powder diffraction (XRPD) pattern as in FIG. 1, wherein the XRPD pattern is expressed in terms of 2 theta angles and obtained with a diffractometer using copper Kα X-radiation, wherein the XRPD pattern comprises 2 theta angle peaks at essentially the following positions: 4.3±0.1, 7.9±0.1, 9.8±0.1, 10.7±0.1, 10.8±0.1, 13.3±0.1, 14.0±0.1, 15.1±0.1 degrees, which correspond respectively to d-spacing at 20.4, 11.1, 9.0, 8.3, 8.2, 6.6, 6.3 and 5.9 Angstroms (Å).

In a fifth aspect of the present invention, there is provided the compound of formula (I) in crystalline anhydrate Form 1, characterized by substantially the same X-ray powder diffraction (XRPD) pattern as in FIG. 1, wherein the XRPD pattern is expressed in terms of 2 theta angles and obtained with a diffractometer using copper Kα X-radiation, wherein the XRPD pattern comprises 2 theta angle peaks at essentially the following positions: 4.3±0.1, 7.9±0.1, 9.8±0.1, 10.7±0.1, 10.8±0.1, 13.1±0.1, 13.2±0.1, 13.3±0.1, 14.0±0.1, 14.4±0.1, 15.0±0.1, 15.1±0.1, 15.7±0.1, 15.9±0.1, 16.3±0.1, 16.5±0.1, 16.8±0.1, 17.0±0.1, 17.4±0.1, 17.5±0.1, 18.1±0.1, 18.2±0.1 18.7±0.1, 19.4±0.1, 19.7±0.1, 20.0±0.1, 20.1±0.1, 20.2±0.1, 20.5±0.1, 20.7±0.1, 21.5±0.1, 21.8±0.1 degrees, which correspond respectively to d-spacings at 20.4, 11.1, 9.0, 8.3, 8.2, 6.8, 6.7, 6.6, 6.3, 6.1, 5.9, 5.9, 5.6, 5.6, 5.4, 5.4, 5.3, 5.2, 5.1, 5.1, 4.9, 4.9, 4.7, 4.6, 4.5, 4.4, 4.4, 4.4, 4.3, 4.3, 4.1 and 4.1 Angstroms (Å).

As a sixth aspect, the present invention provides the compound of formula (I) in crystalline anhydrate Form 1 characterized by substantially the same $^{13}C$ solid state nuclear magnetic resonance (SSNMR) spectrum as in FIG. 3, wherein the SSNMR spectrum was obtained on a spectrometer operating at a frequency of 100.56 MHz for $^{13}C$ observation using a cross-polarization pulse sequence with a Bruker 4-mm triple resonance magic-angle spinning probe at a rotor frequency of 8 kHz.

As a seventh aspect, the present invention provides the compound of formula (I) in crystalline anhydrate Form 1 characterized by SSNMR spectrum obtained on a spectrometer operating at a frequency of 100.56 MHz for $^{13}C$ observation using a cross-polarization pulse sequence with a Bruker 4-mm triple resonance magic-angle spinning probe at a rotor frequency of 8 kHz, wherein the SSNMR comprises chemical shifts at 175.03±0.2, 163.30±0.2, 158.66±0.2, 156.50±0.2, 149.79±0.2, 148.17±0.2, 146.96±0.2, 139.56±0.2, 133.19±0.2, 132.32±0.2, 129.76±0.2, 126.5±0.2, 124.15±0.2, 120.37±0.2, 119.20±0.2, 118.16±0.2, 112.83±0.2, 70.62±0.2, 67.61±0.2, 64.96±0.2, 59.89±0.2, 57.08±0.2, 55.50±0.2, 52.41±0.2, 48.35±0.2, 40.79±0.2, 32.75 and 21.12±0.2. ppm.

As another aspect, the present invention provides a pharmaceutical composition comprising the compound of formula (I) in a crystalline anhydrate form according to the present invention. The pharmaceutical composition may further comprise one or more pharmaceutically acceptable carriers or diluents.

As another aspect, the present invention provides a method for the treatment or prophylaxis of psychotic disorders, depression, mood disorders, anxiety, sleep disorders and substance-related disorders comprising administering to the mammal, an effective amount of the compound of formula (I) in a crystalline anhydrate form according to the present invention.

As another aspect, the present invention provides a method for the treatment or prophylaxis of schizophrenia, depression and alcohol dependence comprising administering to the mammal, an effective amount of the compound of formula (I) in a crystalline anhydrate form according to the present invention.

As another aspect, the present invention provides the compound of formula (I) in a crystalline anhydrate form according to the present invention for use in therapy.

As another aspect, the present invention provides the use of the compound of formula (I) in a crystalline anhydrate form according to the present invention in the preparation of a medicament for the treatment or prophylaxis of psychotic disorders, depression, mood disorders, anxiety, sleep disorders and substance-related disorders.

As another aspect, the present invention provides the compound of formula (I) in a crystalline anhydrate form according to the present invention for use in the treatment or prophylaxis of psychotic disorders, depression, mood disorders, anxiety, sleep disorders and substance-related disorders.

As another aspect, the present invention provides the use of the compound of formula (I) in a crystalline anhydrate form according to the present invention in the preparation of a medicament for the treatment or prophylaxis of schizophrenia, depression and alcohol dependence.

As another aspect, the present invention provides the compound of formula (I) in a crystalline anhydrate form according to the present invention for use in the treatment or prophylaxis of schizophrenia, depression and alcohol dependence.

BRIEF DESCRIPTION OF THE DRAWINGS

FIG. 1 depicts an X-ray powder diffraction (XRPD) pattern of the compound of formula (I) in crystalline anhydrate Form 1 according to the present invention. The XRPD pattern is expressed in terms of 2 theta angles and obtained with a diffractometer using copper Kα X-radiation, according to the procedures described herein.

FIG. 2 depicts a differential scanning calorimetry (DSC) thermogram of the compound of formula (I) in crystalline anhydrate Form 1. The DSC was carried out on a TA Q1000 TA system at a scan rate of 10° C. per minute, using a sample size of between 1 and 2 mg of the compound of formula (I) in crystalline anhydrate Form 1 according to the procedures described herein.

FIG. 3 depicts the solid state NMR (SSNMR) spectrum of the compound of formula (I) in crystalline anhydrite Form 1 according to the present invention. The solid state NMR spectrum was obtained on a spectrometer operating at a frequency of 100.56 MHz for $^{13}C$ observation and a spinning speed of 8 kHz, according to the procedures described herein.

DETAILED DESCRIPTION OF THE INVENTION

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "substantially the same X-ray powder diffraction pattern" is understood to mean that those X-ray powder diffraction patterns having diffraction peaks with 2 theta values within plus or minus 0.1° of the diffraction pattern referred to herein are within the scope of the referred diffraction pattern. In a like manner, the term "at least substantially includes peaks of Table 1" is understood to mean that those X-ray powder diffraction patterns having diffraction peaks with 2 theta values within plus or minus 0.1° of the subject Table are within the scope of the diffraction pattern referenced to the Table 1.

Within the context of the present invention, the terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Within the context of the present invention, the term "psychotic disorder" includes: Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

The term depression and mood disorders includes Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90):

The term anxiety includes Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00):

The term sleep disorders includes primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome.

The term substance related disorders includes Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

We have now found that the compound of formula (I) can be obtained in a crystalline anhydrate form, which surprisingly has particularly good pharmaceutical properties.

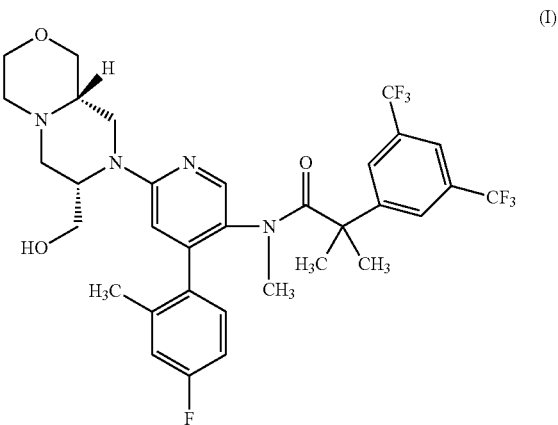 [SMILES: Cc1cc(F)ccc1-c1cc(N2C[C@H]3COCCN3C[C@H]2CO)ncc1N(C)C(=O)C(C)(C)c1cc(C(F)(F)F)cc(C(F)(F)F)c1]

(I)

The wedge shaped bond indicates that the bond is above the plane of the paper. The broken bond indicates that the bond is below the plane of the paper.

The polymorphic forms of the compound of formula (I) may be characterized and differentiated using a number of conventional analytical techniques, including but not limited to X-ray powder diffraction (XRPD), differential scanning calorimetry (DSC) and Solid State NMR (SSNMR).

Polymorphism is defined as the ability of an element or compound to crystallise in more than one distinct crystalline phase. Thus, polymorphs are distinct solids sharing the same molecular formula, however since the properties of any solid depends on its structure, different polymorphs may exhibit distinct physical properties such as different solubility profiles, different melting points, different dissolution profiles, different thermal and/or photostability, different shelf life, different suspension properties and different physiological absorption rate. Inclusion of a solvent in the crystalline solid leads to solvates, and in the case of water as a solvent, hydrates.

Thus, the present invention provides the compound of formula (I) in a crystalline anhydrate form.

In one embodiment, the anhydrate crystalline form of the compound of formula (I) is Form 1.

In another embodiment, the compound of formula (I) in crystalline anhydrate Form 1 is characterized by substantially the same X-ray powder diffraction (XRPD) pattern as in FIG. 1, wherein the XRPD pattern is expressed in terms of 2 theta angles and obtained with a diffractometer using copper Kα X-radiation.

The X-ray powder diffraction (XRPD) pattern of the crystalline anhydrate Form 1 can be determined using conventional techniques and equipment known to those skilled in the art of analytical chemistry and physical characterization. The diffraction pattern of FIG. 1 was acquired on a PANalytical X'Pert Pro powder diffractometer, model PW3050/60, using an X'Celerator detector. The acquisition conditions were: radiation: Cu Kα, generator tension: 45 kV, generator current:

40 mA, step size: 0.008° 2θ, time per step: 575 seconds, divergence slit type: fixed, divergence slit size: 0.4354°, measurement temperature is in the range from 20 to 25° C., goniometer radius: 240 mm. The sample was prepared by packing sample in a 0.7 mm capillary. Characteristic XRPD angles and d-spacings are recorded in Table 1. The margin of error is approximately ±0.1° 2θ for each of the peak assignments.

A powder sample of the crystalline anhydrate Form 1 obtained from Example 1 Method B was used to produce the XRPD pattern of FIG. 1. 2 Theta angles in degrees (x-axis) are plotted against peak intensity in terms of the count rate per seconds (y-axis). The XRD pattern is unique to the particular form; exhibiting a unique set of diffraction peaks which can be expressed in 2 theta angles (°) or d-spacings (Å).

2 Theta diffraction angles and corresponding d-spacing values account for positions of various peaks in the XRD pattern, d-spacing values are calculated with observed 2 theta angles and copper Kα1 wavelength using the Bragg equation. Slight variations in observed 2 theta angles and d-spacings are expected based on the specific diffractometer employed and the analyst's sample preparation technique. More variation is expected for the relative peak intensities. Large variations of relative peak intensities may be observed due to preferred orientation resulting from differences in crystal morphology. Variations in observed 2 theta angles and d-spacings may also be observed depending on the temperature at which the values are measured.

Identification of the exact crystal form of a compound should be based primarily on observed 2 theta angles or d-spacings.

To identify the compound of formula (I) in crystalline anhydrate Form 1, certain characteristic 2 theta angles occur at 4.3±0.1, 7.9±0.1, 9.8±0.1, 10.7±0.1, 10.8±0.1, 13.3±0.1, 14.0±0.1, 15.1±0.1 degrees, which correspond respectively to d-spacing at 20.4, 11.1, 9.0, 8.3, 8.2, 6.6, 6.3 and 5.9 Angstroms (Å).

Although one skilled in the art can identify crystalline anhydrate Form 1 from these characteristic 2 theta angle peaks or d-spacings, in some circumstances it may be desirable to rely upon additional 2 theta angles or d-spacings for the identification of crystalline anhydrate Form 1.

Thus, the compound of formula (I) in crystalline anhydrate Form 1, typically exhibits 2 theta angle peaks at essentially the following positions: 4.3±0.1, 7.9±0.1, 9.8±0.1, 10.7±0.1, 10.8±0.1, 13.1±0.1, 13.2±0.1, 13.3±0.1, 14.0±0.1, 14.4±0.1, 15.0±0.1, 15.1±0.1, 15.7±0.1, 15.9±0.1, 16.3±0.1, 16.5±0.1, 16.8±0.1, 17.0±0.1, 17.4±0.1, 17.5±0.1, 18.1±0.1, 18.2±0.1, 18.7±0.1, 19.4±0.1, 19.7±0.1, 20.0±0.1, 20.1±0.1, 20.2±0.1, 20.5±0.1, 20.7±0.1, 21.5±0.1, 21.8±0.1 degrees, which correspond respectively to d-spacings at 20.4, 11.1, 9.0, 8.3, 8.2, 6.8, 6.7, 6.6, 6.3, 6.1, 5.9, 5.9, 5.6, 5.6, 5.4, 5.4, 5.3, 5.2, 5.1, 5.1, 4.9, 4.9, 4.7, 4.6, 4.5, 4.4, 4.4, 4.4, 4.3, 4.3, 4.1 and 4.1 Angstroms (Å).

Some margin of error is present in each of the 2 theta angle assignments and d-spacings reported above. The error in determining d-spacings decreases with increasing diffraction scan angle or decreasing d-spacing. The margin of error in the foregoing 2 theta angles is approximately ±0.1 degrees for each of the foregoing peak assignments. Since some margin of error is possible in the assignment of 2 theta angles and d-spacings, the preferred method of comparing XRPD patterns in order to identify the particular form of a sample of the compound of formula (I) in crystalline anhydrate Form 1 is to overlay the XRPD pattern of the unknown sample over the XRPD pattern of a known form. For example, one skilled in the art can overlay an XRPD pattern of an unknown sample of the compound of formula (I), obtained using the methods described herein, over FIG. 1 and, using expertise and knowledge in the art, readily determine whether the XRPD pattern of the unknown sample is substantially the same as the XRPD pattern of the compound of formula (I) in crystalline anhydrate Form 1.

Considering 2 theta angles (°) and d-spacing (Å), the compound of formula (I) in crystalline anhydrate Form 1 exhibits the following XRPD pattern characteristics:

TABLE I

| °2 Theta | d-spacing [Å] |
|---|---|
| 4.3 | 20.4 |
| 7.9 | 11.1 |
| 9.8 | 9.0 |
| 10.7 | 8.3 |
| 10.8 | 8.2 |
| 13.1 | 6.8 |
| 13.2 | 6.7 |
| 13.3 | 6.6 |
| 14.0 | 6.3 |
| 14.4 | 6.1 |
| 15.0 | 5.9 |
| 15.1 | 5.9 |
| 15.7 | 5.6 |
| 15.9 | 5.6 |
| 16.3 | 5.4 |
| 16.5 | 5.4 |
| 16.8 | 5.3 |
| 17.0 | 5.2 |
| 17.4 | 5.1 |
| 18.1 | 5.1 |
| 17.5 | 4.9 |
| 18.2 | 4.9 |
| 18.7 | 4.7 |
| 19.4 | 4.6 |
| 19.7 | 4.5 |
| 20.0 | 4.4 |
| 20.1 | 4.4 |
| 20.2 | 4.4 |
| 20.5 | 4.3 |
| 20.7 | 4.3 |
| 21.5 | 4.1 |
| 21.8 | 4.1 |

[1]Margin of error = approx. ±0.1 degrees.

Based upon the foregoing characteristic features of the XRPD pattern the compound of formula (I) in crystalline anhydrate Form 1, one skilled in the art can readily identify the compound of formula (I) in crystalline anhydrate Form 1. It will be appreciated by those skilled in the art that the XRPD pattern of a sample of the compound of formula (I) in crystalline anhydrate Form 1, obtained using the methods described herein, may exhibit additional peaks. The foregoing table provides the most intense peaks which are characteristic of that particular crystalline form. This table does not represent an exhaustive list of peaks exhibited by the compound of formula (I) in crystalline anhydrate Form 1.

The X-ray powder diffraction (XRPD) pattern of Example 1 Method A is consistent with that reported in FIG. 1.

Solid state nuclear magnetic resonance (SSNMR) is another conventional analytical technique for identifying the physical characteristics of the compound of formula (I) in crystalline anhydrate Form 1. The SSNMR spectra of the compound of formula (I) in crystalline anhydrate Form 1 is unique. The solid state NMR spectrum of the compound of formula (I) in crystalline anhydrate Form 1, according to the present invention, is determined using conventional equipment and techniques known to those skilled in the art of analytical chemistry and physical characterization.

$^{13}C$ solid-state NMR data of FIG. 3 was acquired using a Bruker Avance 400 triple-resonance spectrometer operating at a $^1$H frequency of 399.87 MHz. The $^{13}$C SSNMR spectra shown were obtained using a cross-polarization pulse sequence with a Bruker 4-mm triple resonance magic-angle spinning probe at a rotor frequency of 8 kHz. A linear power ramp from 75 to 90 kHz was used on the $^1$H channel to enhance cross-polarization efficiency. Spinning sidebands were eliminated by a five-pulse total sideband suppression pulse sequence. $^1$H decoupling was obtained using the Spinal-64 sequence, while $^{19}$F decoupling was achieved with π-pulse decoupling using one π pulse per rotor period. Characteristic $^{13}$C NMR peak positions are reported relative to tetramethylsilane at 0 ppm (parts per million) and are quoted to a precision of +/−0.2 ppm, because of instrumental variability and calibration.

Certain characteristic chemical shifts observed in the solid state NMR spectrum of the compound of formula (I) in crystalline anhydrate Form 1 using a spectrometer operating at a frequency of 100.56 MHz for $^{13}$C observation at a temperature of 296K, a spinning speed 8 kHz include the following: 175.03±0.2, 163.30±0.2, 158.66±0.2, 156.50±0.2, 149.79±0.2, 148.17±0.2, 146.96±0.2, 139.56±0.2, 133.19±0.2, 132.32±0.2, 129.76±0.2, 126.5±0.2, 124.15±0.2, 120.37±0.2, 119.20±0.2, 118.16±0.2, 112.83±0.2, 70.62±0.2, 67.61±0.2, 64.96±0.2, 59.89±0.2, 57.08±0.2, 55.50±0.2, 52.41±0.2, 48.35±0.2, 40.79±0.2, 32.75 and 21.12±0.2. ppm.

Slight variations in observed chemical shifts are expected based on the specific spectrometer employed and the analyst's sample preparation technique. Some margin of error is present in each of the chemical shifts reported above. The margin of error in the foregoing chemical shifts is approximately ±0.2 ppm.

Since some margin of error is possible in the assignment of chemical shifts, the preferred method of determining whether an unknown form of the compound of formula(I) is crystalline anhydrate Form 1 is to overlay the SSNMR spectrum of the sample over the SSNMR spectrum provided in FIG. 3. One skilled in the art can overlay an NMR spectrum of an unknown sample of the compound of formula(I), obtained using the methods described herein, over FIG. 3 and, using expertise and knowledge in the art, readily determine whether the NMR spectrum of the unknown sample is substantially the same as the NMR spectrum of the compound of formula (I) in crystalline anhydrate Form 1.

Specifically $^{13}$C solid state NMR data of FIG. 3 corresponds to sample of Example 1 Method B of the present patent application.

Any of the foregoing analytical techniques can be used alone or in combination to identify the compound of formula (I) in crystalline anhydrate Form 1. In addition, other methods of physical characterization can also be employed to identify and characterize the compound of formula (I) in crystalline anhydrate Form 1. Examples of suitable techniques which are known to those skilled in the art to be useful for the physical characterization or identification of a crystalline anhydrous form include but are not limited to differential scanning calorimetry (DSC) and infra-red (IR) spectroscopy. These techniques may be employed alone or in combination with other techniques to characterize a sample of an unknown form of the compound of formula (I).

The compound of formula (I) in a crystalline anhydrate form and pharmaceutical compositions comprising the same are useful in therapy, particularly in the treatment or prophylaxis of psychotic disorders, depression, mood disorders, anxiety and sleep disorders in an animal, e.g. a mammal such as a human. The various therapeutic uses disclosed in PCT Publication no. WO07/028654, the subject matter of which is incorporated herein by reference in its entirety, are similarly applicable to the compound of formula (I) in a crystalline anhydrate form.

In another aspect, the present invention provides pharmaceutical compositions comprising an effective amount of the compound of formula (I) in a crystalline anhydrate form.

In another aspect, the present invention provides pharmaceutical compositions comprising an effective amount of the compound of formula (I) in a crystalline anhydrate Form 1, according to the present invention. The pharmaceutical composition may further comprise one or more pharmaceutically acceptable carriers or diluents.

Such pharmaceutical compositions may include one or more pharmaceutically acceptable carriers or diluents. Examples of suitable pharmaceutical compositions and methods for their preparation are described in PCT Publication No. WO07/028654, the subject matter of which is incorporated herein by reference in its entirety. Conveniently, suitable pharmaceutical compositions can be prepared using conventional techniques, and when employed, carriers and diluents. Pharmaceutical compositions for oral administration, such as tablet and capsule formulations, are preferred.

As another aspect, the present invention provides the compound of formula (I) in crystalline anhydrate Form 1 according to the present invention for use in therapy.

As another aspect, the present invention provides the use of the compound of formula (I) in crystalline anhydrate Form 1 according to the present invention in the preparation of a medicament for the treatment or prophylaxis of psychotic disorders, depression, mood disorders, anxiety, sleep disorders and substance-related disorders.

As another aspect, the present invention provides the compound of formula (I) in a crystalline anhydrate Form 1 according to the present invention for use in the preparation of a medicament for the treatment or prophylaxis of schizophrenia, depression, mood disorders and alcohol dependence.

As another aspect, the present invention provides the use of the compound of formula (I) in crystalline anhydrate Form 1 according to the present invention in the treatment or prophylaxis of psychotic disorders, depression, mood disorders, anxiety, sleep disorders and substance-related disorders.

As another aspect, the present invention provides the compound of formula (I) in a crystalline anhydrate Form 1 according to the present invention for use in the treatment or prophylaxis of schizophrenia, depression, mood disorders and alcohol dependence.

The compound of formula (I) as an amorphous form can be prepared according to the method described in PCT Publication No. WO07/028654, the subject matter of which is incorporated herein by reference in its entirety.

Specific methods for the preparation of the specific crystalline anhydrate form of the compound of formula (I) are provided in the following Examples.

The compound of formula (I) in a crystalline anhydrate form for use in the present invention may be used in combination with other therapeutic agents. Similarly, the pharmaceutical formulations of the present invention may include one or more additional therapeutic agents. The various therapeutic agents disclosed in PCT Publication no. WO07/028654, the subject matter of which is incorporated herein by reference in its entirety, that may be combined with the compound of formula (I) or salts thereof are similarly applicable to the compound of formula (I) in a crystalline anhydrate form according to the present invention.

The invention thus provides in a further aspect the use of a combination comprising the compound of formula (I) in a crystalline anhydrate form with a further therapeutic agent to treat or prevent psychotic disorders.

The invention thus provides in a further aspect the use of a combination comprising the compound of formula (I) in a crystalline anhydrate Form 1 with a further therapeutic agent to treat or prevent psychotic disorders.

When the compound of formula (I) in a crystalline anhydrate form is used in combination with other therapeutic agents, the compounds may be administered either sequentially or simultaneously by any convenient route.

When combined in the same formulation it will be appreciated that the two compounds must be stable and compatible with each other and with the other components of the formulation and may be formulated for administration. When formulated separately they may be provided in any convenient formulation, in such a manner as is known for such compounds in the art.

When the compound of formula (I) in a crystalline anhydrate form is used in combination with a second therapeutic agent, the dose of each compound may differ from that when the compounds are used alone. Appropriate doses will be readily appreciated by those skilled in the art.

The following examples are intended for illustration only and are not intended to limit the scope of the invention in any way.

In the procedures that follow, after each starting material, reference to a description is typically provided. This is provided merely for assistance to the skilled chemist. The starting material may not necessarily have been prepared from the batch referred to.

As used herein the symbols and conventions used in these processes, schemes and examples are consistent with those used in the contemporary scientific literature, for example, the *Journal of the American Chemical Society* or the *Journal of Biological Chemistry*.

Specifically, the following abbreviations may be used in the examples and throughout the specification:
g (grams);
mg (milligrams);
L (liters);
mL (milliliters);
µL (microliters);
psi (pounds per square inch);
M (molar);
mM (millimolar);
N (Normal)
kg (kilogram)
i. v. (intravenous);
Hz (Hertz);
MHz (megahertz);
mol (moles);
MIBK (Methyl isobutyl ketone)
w/w (weight/weight)
mmol (millimoles);
RT (room temperature);
min (minutes);
h or hrs (hours);
mp (melting point);
TLC (thin layer chromatography);
$T_r$ (retention time);
RP (reverse phase);
THF (tetrahydrofuran);
DMSO (dimethylsulfoxide);
EtOAc (ethyl acetate);
DME (1,2-dimethoxyethane);
DCM (dichloromethane);
DCE (dichloroethane);
DMF (N,N-dimethylformamide);
HOAc (acetic acid);
Psig (pound-force per square inch gauge)
MTBE (methyl tert-butyl ether)
IPAc (isopropyl acetate)
$Et_3N$ (triethylamine)
wt/vol (weight/volume)
IPA (isopropylalcohol)
loss on drying (LOD)
barg (bar gauge)
rpm (revolutions per minute)
q.s. (quantum sufficiat)
1-propanephosphonic acid anhydride (T3P)
$BH_3$-THF (borane-tetrahydrofuran complex)
HPLC(High Performance Liquid Chromatography).

Unless otherwise indicated, all temperatures are expressed in ° C. (degrees Centigrade). All reactions conducted under an inert atmosphere at room temperature unless otherwise noted.

In the Examples Unless Otherwise Stated:

Proton Magnetic Resonance (NMR) spectra were recorded on Bruker instruments at 400 or 700 MHz, chemical shifts are reported in ppm (δ) using the residual solvent line as internal standard. Splitting patterns are designed as s, singlet; d, double; t, triple; q, quartet; m, multiplet; b, broad. Differential scanning calorimetry (DSC) was carried out on a TA Q1000 calorimeter, at a scan rate of 10° C. per minute. Sample size of between 1 and 2 mg weighed into an aluminum pan, a pan lid placed on top and lightly crimped without sealing the pan.

Intermediate 1

(3R)-4-benzyl-5-oxomorpholine-3-carboxylic acid

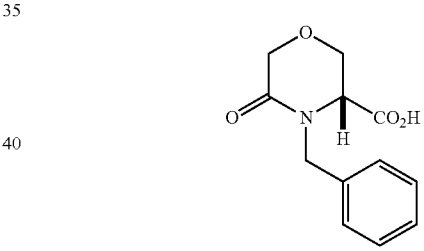

A 300 gallon hastelloy reactor was charged with N-benzyl-D-serine (50.0 kg) followed by the addition of tetrahydrofuran (THF, 271.2 kg). This solution was then cooled to 0° C. and a potassium carbonate (53.1 kg) solution in water (152.5 L) was added in one portion while maintain the temperature between −5° C. and 5° C. The temperature was adjusted back to 0° C. and then chloroacetyl chloride (40.2 kg) was added portion wise over 1 h while keeping the temperature below 4° C. The mixture was stirred for 30 min between 0-4° C. and another portion of chloroacetyl chloride (4.4 kg) was added in one portion. Stirring was continued for and additional 30 min at 0-4° C. A 50% aqueous sodium hydroxide (82.0 kg) solution was added over 50 min while keeping the reaction temperature below 10° C. A final pH endpoint of 13-13.5 should be obtained. After the addition is complete, the solution was cooled to 3-5° C. and stirred at this temperature for 4 h. After determining the reaction was complete (HPLC), it was warmed to 20-22° C. and heptane (75.0 kg) was added and vigorously stirred. The basic aqueous layer was collected, the heptane was removed, and the aqueous layer was placed back into the reactor. The basic aqueous solution was washed once again with heptane (107.8 kg) and placed back into the reactor where it was cooled to 3° C. and then adjusted down to <pH 2.0 by portion wise addition of 12N HCl (193.8 kg) over 1-1.5 h, while keeping the temperature <6° C. After the acid addition was complete, the white solid suspension was cooled to 3-5° C., stirred for an additional 2 h, and then filtered. The cake was then rinsed with cold (3-5° C.) water (50.0 L), pulled dry, and then placed under vacuum at 55-60° C. until the LOD is <0.6% giving the title compound (54.9 kg, 91.2% yield) as a white solid. $^1$H NMR (DMSO-d6) δ 7.37-7.24 (m, 5H), 5.25 (d, J=15.4 Hz, 1H), 4.17 (m, 2H), 4.12 (m 1H), 3.94 (dd, J=5.6, 3.2 Hz, 1H), 3.92 (dd, J=16.8, 3.2 Hz, 1H), 3.82 (d, J=15.4 Hz, 1H).

Intermediate 2

[(3S)-4-benzylmorpholin-3-yl]methanol hydrochloride salt

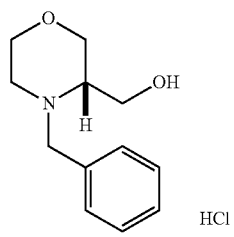 [SMILES: OC[C@H]1COCCN1Cc1ccccc1 ; Cl]

A 500 gallon glass-lined reactor was charged with tetrahydrofuran (401.2 kg) followed by borane-dimethylsulfide complex (10M, 93.1 kg). The solution was heated to 35° C. and then intermediate 1 (47.5 kg) dissolved in tetrahydrofuran (253.4 kg) was added over 1 h maintaining the temperature below 40° C. After the addition, the mixture was stirred for an additional 4 h at 35° C. When the reaction was complete (HPLC), acetone (178.5 kg) was added over 1 h while maintaining the temperature between 35-45° C. The solution was then stirred for an additional 1 h at 35° C. and then warmed to 40° C. and stirred overnight. The following morning, the solution was cooled to 35° C. and water (213.7 L) was added in a controlled manner over 1 h. After the addition was complete, the solution was placed under vacuum and the THF was distilled off to reach a final volume of 238 L. Water (83.1 L) and ethyl acetate (471.3 kg) were added, the solution was heated to 40° C. and then sodium hydroxide (2M, 462 L) was added. The mixture was stirred for 2 min and then allowed to settle. The aqueous was removed and washed again with ethyl acetate (471.3 kg). The two ethyl acetate washes (942.6 kg) were placed back into the reactor and washed with 20% brine solution (199.9 L). The bottom brine layer was removed and discarded. The ethyl acetate solution was placed under vacuum and distilled down to a final volume of 333 L. The solution was cooled to 20° C. and transferred to a clean reactor through a 30 micron Pall filter. The reactor was rinsed with ethyl acetate (85.7 kg) and then the ethyl acetate was passed through the transfer lines and Pall filter. To the filtered ethyl acetate solution was added methanol (172.8 kg). The reaction was cooled to 10° C. and then chlorotrimethylsilane (22.2 kg) was added over 15 min while keeping the temperature below 15° C. The reaction was then cooled to 5° C. and stirred for at least 2 h. The slurry was removed from the reactor and filtered. The wet cake was washed with cold ethyl acetate (64.3 kg), pulled dry and then placed under vacuum at 50-55° C. for 8 h to give the title compound (43.1 kg, 87.6% yield) as a white solid. $^1$H NMR (DMSO-d6) δ 10.88 (br s, 1H), 7.62 (m, 2H), 7.45 (m, 3H), 5.72 (br s, 1H), 4.79 (dd, J=12.9, 2.6 Hz, 1H), 4.19 (dd, J=12.9, 7.5 Hz, 1H), 3.98 (ddd, J=15.4, 12.2, 3.2 Hz, 1H), 3.94-3.81 (m, 3H), 3.78-3.66 (m, 2H), 3.39-3.27 (m, 1H), 3.11-2.97 (m, 1H), 2.89 (d, J=10.8 Hz, 1H).

Intermediate 3

(7S,9aS)-7-[(benzyloxy)methyl]octahydropyrazino[2,1-c][1,4]oxazine dioxalic acid salt

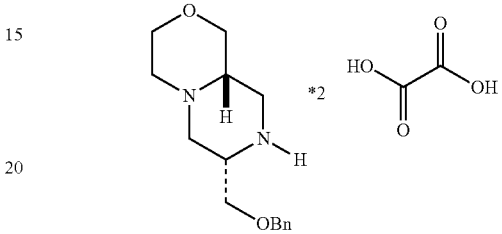

Stage 3a

A 200 gallon high pressure hastelloy reactor was charged with intermediate 2 (42.7 kg) followed by 20% palladium hydroxide (~50% wet) on carbon (4.3 kg). The reactor is sealed and is purged with nitrogen. Ethanol (200 proof, 336.9 kg) was then charged. The agitator was set to maximum allowable speed, the reaction was heated to between 20-30° C., and the reactor was pressurized to 30 psig with hydrogen gas. The hydrogen uptake is monitored for reaction completeness (~3 hrs). After the reaction was complete (HPLC), the ethanol mixture was passed over a Celite packed Pall filter. The filter was then rinsed with an additional amount of ethanol (101.1 kg). The ethanol solutions were combined and used directly for the next reaction. An analytical sample was obtained by evaporation of the ethanol solution to dryness to obtain (S)-1-Morpholin-3-yl-methanol hydrochloride salt. which was then analyzed by NMR. $^1$H NMR (DMSO-d6) δ 9.38 (br s, 1H), 5.43 (t, J=5.2 Hz, 1H), 3.87 (ddd, J=15.5, 12.0, 3.4 Hz, 2H), 3.66 (ddd, J=13.3, 11.0, 2.7 Hz, 1H), 3.61-3.49 (m, 3H), 3.27-3.17 (m, 1H), 3.13 (dt, J=13.0, 2.5 Hz, 1H), 3.02 (ddd, J=14.4, 10.7, 3.7 Hz, 1H).

Stage 3b

A 300 gallon glass-lined reactor was charged with the ethanol solution from stage 3a containing (S)-1-Morpholin-3-yl-methanol hydrochloride salt (579.5 kg based on 100% yield in stage 3a). The solution was distilled down under vacuum to 339 L. The temperature was adjusted to 25° C. and then the reactor was charged with N,N-diisopropylethylamine (69.2 kg) and stirred for 10 min. A solution of N-Boc-O-benzyl-D-serine (42.4 kg) in ethanol (66.9 kg) was then charged into the reactor and stirred at 25° C. for 1 h. After stirring for 1 h, 1-T3P (~50% in ethyl acetate, 114.8 kg) was added portionwise over at least 30 min while maintaining the temperature below 30° C. After the addition, the reaction was stirred at 25° C. for 20 min. When the reaction was complete (HPLC), the reactor was charged with sodium hydroxide (3N, 229.4 kg). The reactor was then placed under vacuum and the ethanol was distilled off to reach a final volume of 339 L. MTBE (470.6 kg) was then added and the mixture was stirred for 10 min and allowed to settle for at least 15 min. The bottom basic aqueous layer was removed and the MTBE was then washed with 1N HCl (256.6 L), 3N sodium hydroxide (256.6 L) and 20% brine solution (213.5 L) respectively. The MTBE layer was removed from the reactor and used directly for the next reaction.

Stage 4.

A 300 gallon glass-lined reactor was charged with the MTBE solution (503.6 kg) from Stage 3b containing [(R)-1-Benzyloxymethyl-2-((S)-3-hydroxymethyl-morpholin-4-yl)-2-oxo-ethyl]carbamic acid tert-butyl ester (48.0 kg). At atmospheric pressure, the MTBE is distilled off to reach a final volume of 144 L. After adjusting the temperature to 25° C., THF (426.7 kg) was added. This solution, at atmospheric pressure, was distilled down to a final volume of 192 L. Again, the solution is cooled to 25° C. and THF (426.7 kg) was added. This solution was distilled down to 144 L under atmospheric pressure, cooled to 25° C. and more THF (57.6 kg) was added back to bring the final solution volume to 193 L. A Karl Fisher analysis was run to determine the amount of water present in solution (additional $BH_3$-THF was added to consume any water detected in solution). A separate (clean, THF rinsed) 500 gallon glass-lined reactor was charged with $BH_3$-THF (1.0M, 327.4 kg) and heated to 35° C. Under nitrogen pressure, the THF solution containing [(R)-1-Benzyloxymethyl-2-((S)-3-hydroxymethyl-morpholin-4-yl)-2-oxo-ethyl]carbamic acid tert-butyl ester was slowly added (at least 2 h) to the $BH_3$-THF solution while maintaining a temperature below 45° C. An additional amount of THF (10.7 kg) was used to wash out the lines and added to reactor. The reaction was maintained at 35° C. for 2.5 hrs and sampled for completeness (HPLC). After the reaction was complete, acetone (49.4 kg) was slowly charged over 1 h while keeping the temperature below 45° C. The reaction was then stirred at least 8 h after which, methanol (113.9 kg) was charged slowly over 1.5 h while keeping the temperature below 45° C. The solution was stirred at 35° C. for 3 h and then, under vacuum, distilled down to 216 L. After adjusting the temperature to 25° C., MTBE (355.2 kg) was added followed by sodium hydroxide (3N, 259.6 kg) over 15 min. The solution was vigorously stirred for 10 min and then allowed to settle. The basic aqueous layer was removed and the MTBE layer was then washed with 20% brine solution (240 L). The brine solution was removed and under vacuum, the MTBE was distilled down to 120 L, cooled to 25° C. and then isopropyl acetate (502.3 kg) was charged to reactor. Under vacuum, the solution was distilled down to 384 L and then removed from the reactor through a 10 micron filter and used directly in the following reaction.

Stage 5a

A 20 L jacketed lined reactor was charged with an isopropyl acetate (3.7 L) solution containing [(S)-1-Benzyloxymethyl-2-((S)-3-hydroxymethyl-morpholin-4-yl)-ethyl]-carbamic acid tert-butyl ester obtained from Stage 4 (0.916 kg assuming a 100% theoretical yield from Stage 4). To this solution was charged DCM (9.2 L) and triethylamine (0.940 L). The solution was cooled to 5° C. and methanesulfonyl chloride (0.690 kg) was added at a rate to keep the temperature below 15° C. After the addition, the reaction was warmed to 20° C. and stirred until deemed complete by HPLC (~20 h). The reaction was quenched with water (4.6 L), stirred for 10 min and then allowed to settle. The aqueous layer was discarded and organic layer was then sequentially washed with 1N HCl (4.6 L) and 5% $NaHCO_3$ (4.6 L). After the washes, the organic layer was distilled down, under vacuum, to 2.8 L. An additional amount of isopropyl acetate (1.8 L) was charged into the reactor and this solution was used directly in the following reaction.

Stage 5b.

A 20 L jacketed lined reactor was charged with 6N HCl (4.58 L) and cooled to 10° C. To this acid solution was added the [(S)-1-Benzyloxymethyl-2-((R)-3-chloromethyl-morpholin-4-yl)-ethyl]-carbamic acid tert-butyl ester solution from Stage 5a at a rate to maintain the temperature below 20° C. The reaction was warmed to 25° C. and stirred until complete by HPLC (~1 h). The stirring was stopped and the two layers were allowed to separate. The bottom acidic layer, was removed and the top organic layer was discarded. The acidic aqueous layer was placed back into the reactor and washed with IPAc (4.6 L). Once again, the aqueous layer was removed and the organic layer was discarded. The reactor was then charged with the aqueous layer followed by IPAc (4.6 L). This mixture was cooled to 2° C. and 50% NaOH (1.154 kg) was added at a rate to maintain the temperature below 20° C. After this addition, the mixture was stirred for 5 min and the pH of the aqueous layer was checked (should be ~7.0). The layers were separated and the bottom aqueous layer was removed and discarded. The top IPAc layer was then reduced down to 3.0 L (3.27 vol) under vacuum distillation. Acetonitrile (10.0 L) was charged into the reactor and this solution was reduced down to 3.0 L under vacuum distillation. Finally an additional amount of acetonitrile (4.5 L) was charged and this solution was used directly in following reaction.

Stage 5c.

A 20 L jacketed lined reactor was charged with acetonitrile (10.8 L) and $Et_3N$ (1.22 kg) and then heated to 60° C. The (S)-1-Benzyloxymethyl-2-((R)-3-chloromethyl-morpholin-4-yl)-ethylamine acetonitrile solution from Stage 5b was added to the reactor over 1 h keeping the temperature of the reaction at approx. 60° C. The mixture was then stirred at 60° C. until the reaction was deemed complete by HPLC. The solution was then concentrated, under vacuum, to 3.0 L. After this distillation, ethyl acetate (2.0 L) was added and the slurry ($Et_3N$.HCl) is cooled to 20° C. The slurry was removed from the reactor and filtered, while collecting and saving the product solution. The $Et_3N$.HCl cake was washed with ethyl acetate (2.8 L). The filtrates containing (7S,9aS)-7-[(benzyloxy)methyl]octahydropyrazino[2,1-c][1,4]oxazine were combined and used directly in Stage 5d. The amount of (7S, 9aS)-7-[(benzyloxy)methyl]octahydropyrazino[2,1-c][1,4]oxazine was determinated by a weight/weight HPLC assay.

Stage 5d

A 20 L jacketed lined reactor was charged with oxalic acid (0.304 kg, 1.0 eq, based on wt/wt HPLC assay of (7S,9aS)-7-[(benzyloxy)methyl]octahydropyrazino[2,1-c][1,4]oxazine solution from Stage 5c), ethanol (200 proof, 2.75 L) and ethyl acetate (6.4 L). The mixture was heated to 60° C. and the crude ethyl acetate solution of (7S,9aS)-7-[(benzyloxy)methyl]octahydropyrazino[2,1-c][1,4]oxazine from Stage 5C was added to the reactor at a rate to maintain the temperature above 50° C. This solution was stirred at 60° C. for 30 min, cooled to 20° C. and then stirred overnight at 20° C. The solids were removed, filtered and then washed with an ethyl acetate: ethanol (6:1, 1.8 L) solution. The solids were then placed in an oven, under vacuum, at 50° C., until dry, giving the title compound as a beige crystalline solid (0.306 kg). A second crop of the title compound was obtained from the mother liquor (0.133 kg). $^1$H NMR (DMSO-d6) δ 9.5-8.5 (br s, 4H) 7.41-7.36 (m, 3H), 7.35-7.27 (m, 2H), 4.57 (d, J=2.0 Hz, 2H), 3.94 (t, J=8.3 Hz, 1H), 3.76-3.61 (m, 4H), 3.45 (ddd, J=13.9, 11.7, 2.2 Hz, 1H), 3.06 (t, J=11.8 Hz, 1H), 2.94 (dd, J=12.7, 2.9 Hz, 1H), 2.79 (d, J=12.4 Hz, 1H), 2.67 (t, J=12.5 Hz, 1H), 2.56 (d, J=11.4, 1H), 2.43 (dd, J=12.7, 3.4 Hz, 1H), 2.39-2.29 (m, 1H), 2.14 (ddd, J=14.9, 11.5, 3.2 Hz, 1H).

Intermediate 4

2-[3,5-bis(trifluoromethyl)phenyl]-N-{4-(4-fluoro-2-methylphenyl)-6-[(7S,9aS)-7-{[(phenylmethyl)oxy]methyl}hexahydropyrazino[2,1-c][1,4]oxazin-8(1H)-yl]-3-pyridinyl}-N,2-dimethylpropanamide dihydrochloride salt

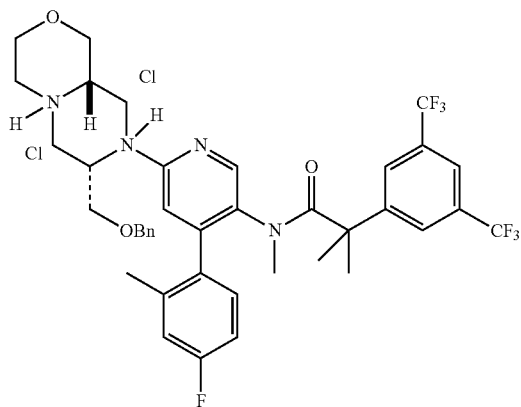

A 100 gallon glass-lined reactors was charged with intermediate 3(10.5 kg), toluene (173 kg) and 1N NaOH (200 L). This biphasic mixture was heated to 75° C. and stirred for 5 min. The stirring was stopped and the layers were allowed to settle for 30 min. At 75° C., the bottom basic aqueous layer was removed. After cooling to 25° C., water (100 L) was added and stirred for 10 min. The mixture was allowed to settle for 15 min and the bottom aqueous layer was removed. The toluene layer was concentrated under vacuum to 40 L and then 34.6 kg of fresh toluene was added. This solution was tested for its water content by Karl Fisher analysis (<0.05% wt/vol). After the solution is tested for water content, more toluene (77.9 kg) was added giving a final solution volume of 180 L. In a separate 100 gallon glass-lined reactor, ((2-[3,5-bis(trifluoromethyl)phenyl]-N-[6-chloro-4-(4-fluoro-2-methylphenyl)-3-pyridinyl]-N,2-dimethylpropanamide (10.0 kg) was charged followed by sodium t-butoxide (3.2 kg) and palladium (0) bis-tri-t-butylphosphine (0.957 kg). The toluene solution of intermediate 3 was then added to these solids and heated to 85° C. The reaction was stirred at 85° C. until the reaction was complete by HPLC (~2-4 h). The solution was cooled to 25° C. and then a 20% aq. NaHSO₃ (100 L) solution was charged into the reactor. The biphasic mixture was heated to 60° C., stirred for 1 h and cooled back to 25° C. This biphasic mixture was removed from the reactor and filtered over a Celite packed Pall filter. The filter was rinsed with toluene (8.7 kg), combined with the initial filtrate and placed back into the reactor to settle for 30 min. After settling, the bottom aqueous layer was removed and discarded. The reactor was then charged with 5% aq. cysteine (100 L,) solution. The mixture was heated to 60° C., stirred for 1 h and then cooled to 25° C. Once again, this biphasic mixture was removed from the reactor and filtered over a Celite packed Pall filter. The filter was rinsed with toluene (8.7 kg) and the combined filtrates were placed back into the reactor and 10% aq sodium chloride (40 kg) was added. The mixture was stirred for 15 min and allowed to settle for 30 min. The bottom aqueous layer was removed and discarded. The reactor was then charged with 5% aq. cysteine (100 L) solution. The mixture was heated to 60° C., stirred for 1 h and then cooled to 25° C. The biphasic mixture was removed from the reactor and filtered over a Celite packed Pall filter. The filter was rinsed with toluene (8.7 kg) and the combined filtrates were placed back into the reactor and 10% aq sodium chloride (40 kg) was added. The mixture was stirred for 15 min and allowed to settle for 30 min. The bottom aqueous layer was removed and discarded. A 5% aq. sodium bicarbonate (70 L) solution was added to the toluene layer and stirred for 10 min. The layers were allowed to settle for 30 min and the bottom bicarbonate layer was removed and discarded. A 2% aq. sodium chloride (70 L) solution was added and stirred for 15 min. The mixture was allowed to settle for 30 min and the bottom aqueous layer was removed and discarded. A second 2% aq. sodium chloride (70 L) solution was added and stirred for 15 min. The mixture was allowed to settle for 30 min and the bottom aqueous layer was removed and discarded. The top toluene layer was concentrated under vacuum distillation to 40 L and then an additional amount of toluene (60.6 kg) was added. The water content of this solution was tested using Karl Fisher analysis (<1.0% wt/vol). The reactor was then charged with 4N HCl in dioxane (10.3 kg) and stirred at 25° C. for 30 min. After stirring was finished, toluene (77.9 kg) was added and the solution was distilled, under vacuum, to a final volume of 100 L. More toluene (77.9 kg) was charged and the solution is again reduced under vacuum to a final volume of 100 L. A sample was taken for Gas Chromatography analysis to determine the content of 1,4-dioxane in solution (<0.55% 1,4-dioxane). The temperature of the solution was adjusted to 25° C. and n-heptane (47.9 kg) was slowly added to the reactor over at least 30 min. The slurry was stirred at 25° C. at least 4 h. The solids were removed from the reactor and filtered. The filter cake was washed with 27.4 kg of n-heptane. The solids were then placed in a vacuum oven at 40° C. overnight to give the title compound (12.3 kg, 78.8% yield) as a tan solid.

¹H NMR (DMSO-d6) δ 8.02 (s, 1H), 7.95 (s, 1H), 7.73 (br s, 2H), 7.27 (m, 5H), 7.18 (s, 1H), 7.16 (s, 1H), 7.11 (br s, 1H), 6.83 (s, 1H), 5.12 (br m, 6H), 4.64 (d, J=12.5 Hz, 1H), 4.50 (d, J=11.7 Hz, 1H), 4.41 (m, 1H), 4.31-4.14 (m, 2H), 4.05-3.76 (m, 4H), 3.60 (d, J=12.7 Hz, 1H), 3.51-3.39 (m, 2H), 3.35-3.12 (m, 2H), 3.12-3.0 (m, 1H), 2.55 (m, 1H), 2.36-1.96 (m, 4H), 1.56-1.15 (m, 4H).

Intermediate 5

2-[3,5-bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide dihydrochloride salt mono-isopropanol solvate

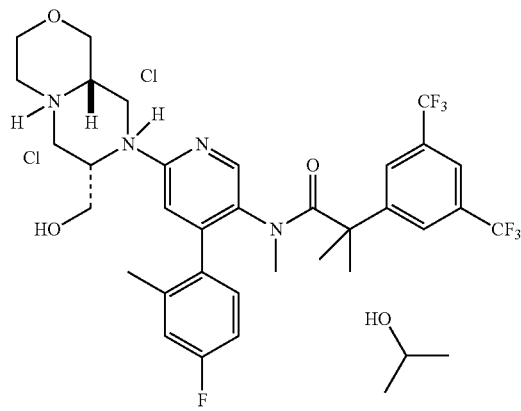

A 20 L jacketed lined reactor was charged with intermediate 4 (1.12 kg), 10% palladium on carbon, ~50% wet, (0.225 kg), isopropanol (10.08 L), water (1.12 L) and concentrated hydrochloric acid (0.140 kg). This mixture was vigorously stirred, heated to 50° C. and placed under 0.25 barg of hydrogen pressure until the reaction was deemed complete by HPLC (~3.5-5 h). After the reaction was complete, the reactor was purged with nitrogen and cooled to 25° C. The reaction was drained from the reactor and filtered through a Celite packed Pall filter to remove the palladium catalyst. Isopropanol (10.1 L) and water (1.12 L) were added to reactor and then passed through the Pall filter. The filtrates were combined to give the title compound in isopropanol solution (~24.0 L). Another reaction, using equivalent amounts, was run and combined to give the title compound (2.16 kg) in isopropanol solution (48.0 L). These combined solutions were charged into a 50 L jacketed lined reactor through a 0.45 micron filter. The solution was distilled down, under vacuum, to 8.0 L and then additional IPA (22.4 L) was charged into the reactor. This solution was again distilled down, under vacuum, to 8.0 L and more IPA (22.4 L) was added. Once again, the solution was reduced down to 8.0 L and IPA (19.1 L) was added. A sample was taken and tested for water content using Karl Fisher analysis (<0.4% wt/vol). The solution is adjusted to 25° C. and 4N HCl in dioxane (1.35 L) was added. The reaction was then heated to 65° C. and stirred for 30 min. The solution was cooled to 25° C. and 2,2,4-trimethylpentane (11.2 L) was added and the slurry was stirred overnight. The solids were removed from the reactor and filtered. The filter cake was washed with a 1/1 solution (5.0 L) of IPA and 2,2,4-trimethylpentane. The solids were blown dry and placed into a vacuum oven at 30° C. overnight giving the title compound (1.914 kg, 88.6% yield) as a pale white solid. $^1$H NMR (DMSO-d6) δ 11.42 (br s, 1H), 8.01 (s, 1H), 7.97 (br s, 1H), 7.73 (br s, 2H), 7.18 (d, J=10.2 Hz, 1H), 7.12 (br m, 2H), 6.95 (s, 1H), 5.78 (br s, 5H), 4.77-4.65 (m, 1H), 4.57-4.43 (m, 1H), 4.21 (dd, J=12.7, 1.2 Hz, 1H), 4.06-3.81 (m, 5H), 3.77 (sept, J=6.1 Hz, IPA, 1H), 3.64 (d, J=12.7 Hz, 1H), 3.52-3.42 (m, 1H), 3.42 (d, J=11.7 Hz, 1H), 3.29 (dd, J=12.4, 4.4 Hz, 1H), 3.24-3.09 (m, 2H), 2.65-2.54 (m, 1H), 2.38-2.05 (m, 4H), 1.56-1.11 (m, 4H), 1.03 (d, J=6.2 Hz, IPA, 6H).

Example 1

Preparation of 2-[3,5-bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide in crystalline anhydrate Form 1

Method A 8 g of of 2-[3,5-bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide as amorphous free base, was dispensed into a foil covered 500 mL vessel. The solid was slurried in 120 ml of Iso octane, in a polyblock, with overhead stirring at 350 rpm. The slurry was heated to 70° C. at a rate of 5° C./min. Within 15 minutes the mobile slurry had changed colour from pale yellow to cream. After 1 night at 70° C. the slurry was cooled to 25° C. at 1° C./min. Solid was isolated by filtration under vacuum using a porosity 3 filter. A pale yellow, damp powder, filter dried to give a cream powder (solid 1).

Some material could not be filtered since it had formed an agglomerate ball in the vessel. The previously collected filtrate was re-dispensed into the vessel. The agglomerated material was left to disperse into a slurry by stirring at 70° C. for 7 hrs. The experiment was then cooled to 25° C. at 1° C. min and held there for 3 nights. On filtration a cream powder was obtained (solid 2).

Solids 1 and 2 were dried at 40° C. under vacuum for 19 hrs to obtain the title compound (7.087 g).

Method B

A 100 gallon glass-lined reactor was charged with intermediate 5 (10.1 kg) followed by MTBE (112.1 kg). To this mixture was added 2.5N NaOH (50.5 L). The reaction was stirred until it reached 40° C. and then allowed to settle for 15 min at 40° C. The bottom aqueous layer was removed and discarded. The reactor was then charged with a 10% L-cysteine (50.5 L) aqueous solution. This biphasic mixture was heated to 40° C. and stirred for 1 h. The mixture was allowed to settle for 15 min and the bottom aqueous layer was removed and discarded. The reactor was then charged with water (50.5 L). The mixture was stirred at 40° C. for 15 min, allowed to settle for 60 min and the bottom aqueous layer removed and discarded. Again, water (50.5 L) was charged and the reaction stirred at 40° C. for 15 min and then allowed to settle for 60 min. The bottom layer was removed and discarded. The MTBE layer was distilled down at atmospheric pressure to ~25 L. The MTBE solution was warmed to 55° C. and then 2,2,4-trimethylpentane (58.3 kg) was added slowly over 1 h while maintaining the temperature between 50-55° C., the solution was then heated, at atmospheric pressure, until the final volume was approximately 40 L. The solution was then cooled to 75° C. and IPA (6.0 kg,) was added to the reactor. This solution was cooled to 55° C. and then passed through a cartridge filter into a clean 100 gallon glass-lined reactor. Through a cartridge filter, additional 2,2,4-trimethylpentane (31.1 kg) was added to the reactor. After the addition, the solution was heated to 70° C., stirred for 30 min, and then cooled back to 50° C. A seed slurry of 2-[3,5-bis(trifluoromethyl)phenyl]-N-{4-(4-fluoro-2-methyl phenyl)-6-[(7S,9aS)-7-(hydroxymethyl)hexahydropyrazino[2,1-c][1,4]oxazin-8(1H)-yl]-3-pyridinyl}-N,2-dimethylpropanamide in crystalline anhydrate Form 1 (0.0838 kg) in IPA (0.0657 kg) and 2,2,4-trimethylpentane (0.5222 kg) was prepared using solvents filtered through a cartridge filter. This seed slurry was then charged to the reactor at 50° C. The slurry was then stirred at 50° C. for at least 3 h. 2,2,4-trimethylpentane (29.2 kg) was then added to the reactor (through a cartridge filter) over 3 h, via a metering pump. After this addition was complete, the slurry was then held at 50° C. overnight, then cooled to 0° C. over 4.5 h and then held at 0° C. for at least 3 h. The slurry was then removed and filtered via filter dryer. The filter cake was then washed 2 times with cold (0° C.). 2,2,4-triemthylpentane (2×23.3 kg) that had been passed through a cartridge filter into the reactor. The solids were dried in the filter dryer under vacuum at 50° C. (LOD<0.5%) for 15 h. The solids were then removed from the dryer and screened via a Quadro® Comil®, C-101 and collected in a HDPE (high density polyethylene) drum double lined with polyethylene bags to give the title compound (6.1 kg, 72.6% yield) as a white solid.

Onset melt combined with degradation=162° C. by DSC.
$^1$H NMR (DMSO-d6) δ 8.01 (s, 1H), 7.85 (s, 1H), 7.73 (br s, 2H), 7.15 (d, J=10.0 Hz, 1H), 7.11 (br m, 2H), 6.60 (s, 1H), 4.68 (dd, J=6.4, 1.7 Hz, 1H), 4.27-4.16 (m, 1H), 4.16-4.0 (m, 1H), 3.81-3.69 (m, 3H), 3.55 (dd, J=11.7, 2.0 Hz, 1H), 3.45-3.36 (m, 1H), 3.15 (t, J=10.5 Hz, 1H), 3.02 (d, J=10.7 Hz, 1H), 2.64 (d, J=11.8 Hz, 1H), 2.58-2.53 (m, 2H), 2.32-2.01 (m, 8H), 1.57-1.12 (m, 6H).

X-Ray Powder Diffraction (XRPD)

The XRPD pattern was acquired on a a PANalytical X'-Pert Pro powder diffractometer model PW3050/60 using an X'Celerator detector equipped with a monochromator using copper Kα X-radiation. The acquisition conditions were: radiation: Cu Kα, generator tension: 45 kV, generator current: 40 mA, step size: 0.008° 2θ, time per step: 575 seconds, divergence slit type: fixed, divergence slit size: 0.4354°, measurement temperature is in the range from 20 to 25° C., goniometer radius: 240 mm. The sample was prepared by packing few milligrams of Example 1 Method B in a 0.7 mm capillary.

The Pattern is provided in FIG. 1.

The X-ray powder diffraction (XRPD) pattern of Examples 1 Method A is consistent with that reported in FIG. 1.

Thermal Analysis.

Differential scanning calorimetry (DSC) was carried out on a TA Q1000 calorimeter. The sample of Example 1 Method B was weighed into an aluminum pan, a pan lid placed on top and light crimped without sealing the pan. Scan rate of 10° C. per minute. Sample size of between 1 and 2 mg. The thermogram of the compound of formula (I) in crystalline anhydrate Form 1 is provided at FIG. 2.

Differential scanning calorimetry (DSC) thermogram of Examples 1 Method A is consistent with that reported in FIG. 2.

When reporting DSC data, the onset or peak temperature of an event can be reported. In the current filling, onset temperatures are only reported. The onset temperature is the intersection of the leading event tangent with the baseline.

Moderately sharp asymmetric melting endotherm with onset temperature of 162° C. combined with the decomposition.

When the melt is combined with the degradation, the person skill in the art will appreciate that small variation in the onset melt temperature may be observed with different batches of the same material.

Solid State Nuclear Magnetic Resonance.

$^{13}$C solid-state NMR spectrum of Example 1 Method B is provided in FIG. 3. Data was acquired using a Bruker Avance 400 triple-resonance spectrometer operating at a $^1$H frequency of 399.87 MHz. The $^{13}$C SSNMR spectra shown were obtained using a cross-polarization pulse sequence with a Bruker 4-mm triple resonance magic-angle spinning probe at a rotor frequency of 8 kHz. A linear power ramp from 75 to 90 kHz was used on the $^1$H channel to enhance cross-polarization efficiency. Spinning sidebands were eliminated by a five-pulse total sideband suppression pulse sequence. $^1$H decoupling was obtained using the Spinal-64 sequence, while $^{19}$F decoupling was achieved with π-pulse decoupling using one π pulse per rotor period. Characteristic $^{13}$C NMR peak positions are reported relative to tetramethylsilane at 0 ppm (parts per million) and are quoted to a precision of +/−0.2 ppm, because of instrumental variability and calibration.

Pharmaceutical Compositions

The compound of formula (I) in crystalline anhydrate Form 1 will normally, but not necessarily, be formulated into pharmaceutical compositions prior to administration to a patient. In one aspect, the invention is directed to pharmaceutical compositions comprising the compound of formula (I) in crystalline anhydrate Form 1.

Tablets of the compound of formula (I) in crystalline anhydrate Form 1 have been formulated as brownish yellow, film-coated round (or oblong for the 200 mg strength) tablets containing 20 mg, 25 mg, 45 mg, 100 mg and 200 mg of the compound of formula (I) in crystalline anhydrate Form 1 which provide an immediate release of the active ingredient for oral administration.

The list of excipients and quantitative composition of tablets are reported in Table 2 below.

TABLE 2

Composition of Tablets of the compound of formula (I) in crystalline anhydrate Form 1

| Component | Quantity (mg/tablet) Tablet Strength | | | | | | Function |
|---|---|---|---|---|---|---|---|
| | 20 | 25 | 45 | 100 | 150 | 200 | |
| Tablet core | | | | | | | |
| The compound of formula (I) in crystalline an hydrate Form 1 | 20.00 | 25.00 | 45.00 | 100.00 | 150.00 | 200.00 | Active ingredient |
| Microcrystalline cellulose | 100.00 | 81.11 | 100.00 | 114.45 | 196.67 | 218.89 | Filler |
| Lactose | 257.50 | 226.28 | 232.50 | 107.11 | 255.67 | 176.22 | Filler |
| Croscarmellose sodium | 13.50 | 11.33 | 13.50 | 13.83 | 24.50 | 26.17 | Disintegrant |
| Hypromellose | 5.00 | 2.78 | 5.00 | 11.11 | 16.67 | 22.22 | Binder |
| Magnesium stearate | 4.00 | 3.50 | 4.00 | 3.50 | 6.50 | 6.50 | Lubricant |
| Purified water[1] | q.s. | q.s. | q.s. | q.s. | q.s. | q.s. | Granulating Fluid |
| Film coat | | | | | | | |
| Opadry ® Yellow 03B22133 | 12.00 | 10.5 | 12.00 | 10.5 | 19.50 | 19.50 | Coating agent |
| Purified water[1] | q.s. | q.s. | q.s. | q.s. | q.s. | q.s. | Suspending agent |

[1]Removed during processing. Does not appear in the final product.

The compound of formula (I) in crystalline anhydrate Form 1 tablets, 20 mg, 25 mg, 45 mg, 100 mg and 200 mg were manufactured using wet granulation, dry blending, tablet compression and film coating processes.

Drug substance, lactose monohydrate, microcrystalline cellulose and croscarmellose sodium were sieved and dry mixed into the high shear mixer granulator for approximately 5 minutes. The granulation water was sprayed onto the drug substance, lactose monohydrate, microcrystalline cellulose and croscarmellose sodium dry blend. The wet granule was dried approximately at 65° C. into a fluid bed dryer for approximately 40 minutes (<2% LOD), milled using a conical mill (screen size 813 μm) and blended into a bin blender with lactose, microcrystalline cellulose and croscarmellose sodium for approximately 20 minutes. Magnesium stearate was added for lubrication into the bin blender and the mixture was blended for approximately 3 minutes.

The blend was compressed using a suitable alternative (monopunch) tablet compression machine to obtain uncoated tablets. Opadry® Yellow 03B22133 was charged into a mixing vessel with purified water and the film coating suspension prepared with stirring. The tablets were film coated into a suitable pan coater (approximately 3% weight gain).

What is claimed is:

1. A compound of formula (I):

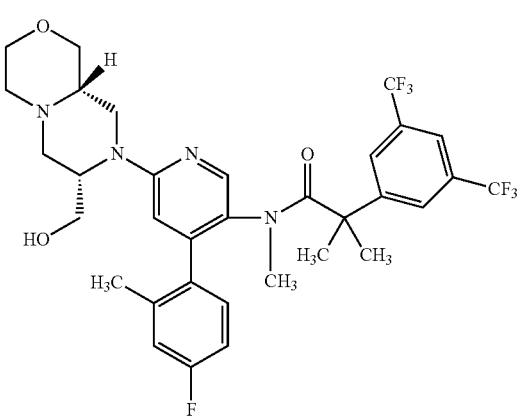

(I)

in a crystalline anhydrate form and having an X-ray powder diffraction pattern comprising 2 theta angle peaks at 7.9°±0.1, 9.8°±0.1, and 10.8°±0.1 which correspond respectively to d-spacing at 11.1, 9.0, and 8.2 Å.

2. The compound according to claim 1, having substantially the same X-ray powder diffraction pattern as in FIG. 1.

3. The compound according to claim 1, having an X-ray powder diffraction pattern comprising 2 theta angle peaks at the following positions: 4.3°±0.1, 7.9°±0.1, 9.8°±0.1, 10.7°±0.1, 10.8°±0.1, 13.3°±0.1, 14.0°±0.1, 15.1±0.1° degrees, which correspond respectively to d-spacing at 20.4, 11.1, 9.0, 8.3, 8.2, 6.6, 6.3 and 5.9 Å.

4. The compound according to claim 1, having an X-ray powder diffraction pattern comprising 2 theta angle peaks at the following positions: 4.3°±0.1, 7.9°±0.1, 9.8°±0.1, 10.7°±0.1, 10.8°±0.1, 13.1°±0.1, 13.2°±0.1, 13.3°±0.1, 14.0°±0.1, 14.4°±0.1, 15.0°±0.1, 15.1°±0.1, 15.7°±0.1, 15.9°±0.1, 16.3°±0.1, 16.5°±0.1, 16.8°±0.1, 17.0°±0.1, 17.4°±0.1, 17.5°±0.1, 18.1°±0.1, 18.2°±0.1, 18.7°±0.1, 19.4°±0.1, 19.7°±0.1, 20.0°±0.1, 20.1°±0.1, 20.2°±0.1, 20.5°±0.1, 20.7°±0.1, 21.5°±0.1, and 21.8±0.1° degrees, which correspond respectively to d-spacings at 20.4, 11.1, 9.0, 8.3, 8.2, 6.8, 6.7, 6.6, 6.3, 6.1, 5.9, 5.9, 5.6, 5.6, 5.4, 5.4, 5.3, 5.2, 5.1, 5.1, 4.9, 4.9, 4.7, 4.6, 4.5, 4.4, 4.4, 4.4, 4.3, 4.3, 4.1 and 4.1 Å.

5. The compound according to claim 1, having a $^{13}C$ solid state nuclear magnetic resonance spectrum comprising chemical shifts at 175.03±0.2, 163.30±0.2, 158.66±0.2, 156.50±0.2, 149.79±0.2, 148.17±0.2, 146.96±0.2, 139.56±0.2, 133.19±0.2, 132.32±0.2, 129.76±0.2, 126.5±0.2, 124.15±0.2, 120.37±0.2, 119.20±0.2, 118.16±0.2, 112.83±0.2, 70.62±0.2, 67.61±0.2, 64.96±0.2, 59.89±0.2, 57.08±0.2, 55.50±0.2, 52.41±0.2, 48.35±0.2, 40.79±0.2, 32.75 and 21.12±0.2 ppm.

6. A pharmaceutical composition comprising the compound according to claim 1 and a pharmaceutically acceptable carrier and/or diluent.

7. A pharmaceutical composition according to claim 6 further comprising one or more additional pharmaceutically acceptable carriers or diluents.

8. A method for the treatment or prophylaxis of psychotic disorders, depression, mood disorders, anxiety, sleep disorders and alcohol dependence comprising administering to the mammal, an effective amount of the compound according to claim 1.

9. A compound of formula (I):

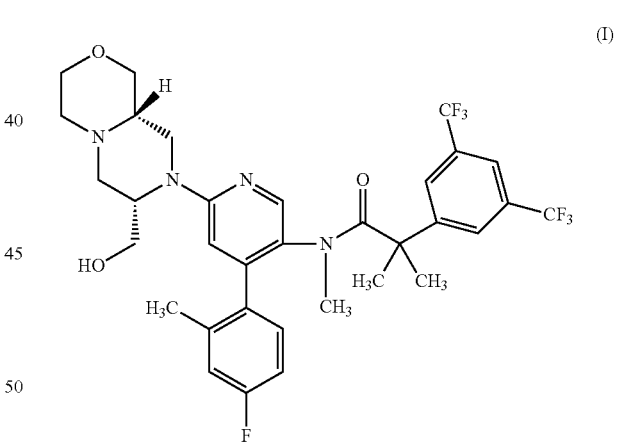

(I)

in crystalline anhydrate form, having the same $^{13}C$ solid state nuclear magnetic resonance spectrum as in FIG. 3.

* * * * *